United States Patent [19]

Wong et al.

[11] Patent Number: 4,585,861
[45] Date of Patent: Apr. 29, 1986

[54] 1,2,4-TRIAZINE DERIVATIVES

[75] Inventors: David T. Wong; William B. Lacefield, both of Indianapolis, Ind.

[73] Assignee: Eli Lilly and Company, Indianapolis, Ind.

[21] Appl. No.: 688,946

[22] Filed: Jan. 4, 1985

Related U.S. Application Data

[62] Division of Ser. No. 354,982, Mar. 5, 1982, Pat. No. 4,513,135.

[51] Int. Cl.⁴ .................. C07D 401/04; C07D 413/04
[52] U.S. Cl. .................................... 544/182; 544/112; 260/243.3

[58] Field of Search ............................. 544/182, 112; 260/243.3

[56] References Cited

U.S. PATENT DOCUMENTS 4,008,232  2/1977  Lacefield ............................. 544/182
4,013,654  3/1977  Lacefield ............................. 544/182
4,190,725  2/1980  Lacefield ............................. 544/182

Primary Examiner—John M. Ford
Attorney, Agent, or Firm—Charles W. Ashbrook; Arthur R. Whale

[57] ABSTRACT

This invention relates to certain amino-5,6-diaryl-1,2,4-triazines and -pyrazines useful as activators of GABA and benzodiazepine binding.

19 Claims, No Drawings

1,2,4-TRIAZINE DERIVATIVES

This application is a division of application Ser. No. 354,982, filed Mar. 5, 1982, now U.S. Pat. No. 4,513,135.

BACKGROUND OF THE INVENTION

Gamma-aminobutyric acid (GABA) is recognized as a major inhibitory neurotransmitter of the mammalian central nervous system. The discovery of specific receptors for GABA and for the benzodiazepines in 1977 was followed by discovering the interaction of the two receptors in 1978. These findings provide the first biochemical evidence for the support of a long-standing belief that some of the therapeutic effects of the benzodiazepines result from a facilitation of GABA receptor function.

Many clinical conditions are thought to arise, in part, from the imbalance between neurotransmission of GABA and those of other neurotransmitters. These conditions include Huntington's chorea, Parkinson's disease, spasticity, epilepsy, schizophrenia and tardive dyskinesia. Decreased GABA activity appears to contribute to the pathogenesis of these diseases. In addition, analgesia and satiety are thought to be regulated by GABA activity. Methods of modifying GABAergic neurotransmission are therefore desirable in order to modify these conditions.

Reduced GABA neuronal function can occur by the inhibition of GABA synthesis, by the blocking of the GABA receptors, or by the inhibition of chloride permeability. By reversing any or all of these functions, a therapeutic effect is possible. For instance, GABA agonists (which stimulate the GABA receptor), compounds which decrease GABA metabolism, and compounds which activate the GABA receptor by stimulating the benzodiazepine receptor have all been reported to inhibit a variety of induced seizure states. Several drugs, such as the benzodiazepines and progabide, have been found to be clinically effective as anticonvulsive agents, although many are limited or prevented in their use because of toxicity or secondary effects.

It is the object of this invention to provide novel compounds which demonstrate an ability to increase GABA and benzodiazepine binding and which also provide a therapeutic benefit in mammals having conditions derived from decreased GABA neuronal function but which avoid certain side effects and other undesirable attributes of compounds currently available for these disease states.

SUMMARY OF THE INVENTION

The present invention is directed to compounds of the formula

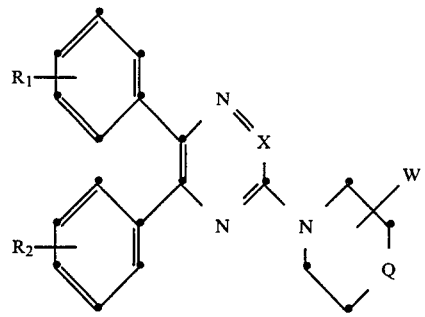

wherein
each $R_1$ $R_2$ is independently $C_1$-$C_3$ alkyl or chloro;
X is CH or N;
Q is oxygen or —$(CH_2)_n$—, where n is 0, 1, or 2;
W is hydrogen, $C_1$-$C_3$ alkyl, $C_1$-$C_3$ alkoxy, keto, hydroxyimino, (—$OCH_2$)$_2$, hydroxy, hydroxymethyl, —OCHO, —OCOA, —$OSO_2$A, or —COB, where A is $C_1$-$C_4$ alkyl, phenyl, phenoxy, amino, $C_1$-$C_3$ alkyl substituted phenyl, or mono- or di-$C_1$-$C_3$ alkyl amino, and where B is $C_1$-$C_3$ alkoxy, amino, or mono- or di-$C_1$-$C_3$ alkyl amino; subject to the limitations that when Q represents oxygen, W is limited to hydrogen, and that when Q represents —$(CH_2)_n$—, W, except when hydrogen or $C_1$-$C_3$ alkyl, is not on a carbon atom adjacent to the ring nitrogen atom.

The compounds of this invention are useful as activators of GABA and benzodiazepine receptor binding and in the treatment of GABA related disease states.

DETAILED DESCRIPTION OF THE INVENTION

The term "$C_1$-$C_3$ alkyl" includes methyl, ethyl, n-propyl, and isopropyl. The term "$C_1$-$C_4$ alkyl" includes methyl, ethyl, n-propyl, isopropyl, n-butyl, sec-butyl, and tert-butyl. The term "$C_1$-$C_3$ alkoxy" includes methoxy, ethoxy, n-propoxy, and isopropoxy.

The starting materials, intermediates and compounds of the invention are prepared by methods known to the art. The preparation of 5,6-diaryl-1,2,4-triazines is described by John G. Erickson in "The 1,2,3- and 1,2,4-Triazines, Tetrazines and Pentazines," *The Chemistry of Heterocyclic Compounds*, Vol. 10, Interscience Publishers, Inc., New York, N.Y., 1956, Chapter II, pp 44–84. The preparation of the 3-amino-5,6-diaryl-1,2,4-triazines by means of the amine nucleophilic displacement of a labile group at the 3-position of a 3-substituted-5,6-diaryl-1,2,4-triazine is known to the triazine and related pyrimidine art [see *J. Amer. Chem. Soc.*, 78, 217 (1956)]. Alternatively, the compounds of the invention may be prepared by the condensation of 3,3-disubstituted aminoguanidines with the appropriate benzils.

According to the first method the 3-amino-5,6-diaryl-1,2,4-triazine compounds of this invention are prepared by reacting a 3-chloro-, 3-methoxy- or 3-methylmercapto-5,6-diaryl-1,2,4-triazine precursor with amines via nucleophilic displacement of the labile group on the 3-position. The starting materials in this method are prepared as follows: The appropriate benzil starting materials are condensed with semicarbazide or its hydrochloride to provide 3-hydroxy-5,6-diaryl-1,2,4-triazine intermediates. The 3-hydroxytriazines are converted to the corresponding 3-chlorotriazines by reaction with phosphorous oxychloride. Methanolysis of the 3-chlorotriazines under basic conditions provides the respective 3-methoxytriazine intermediates. Benzil condensations with thiosemicarbazide provide 5,6-diaryl-1,2,4-triazine-3-thiols which are converted to the corresponding 3-methylmercaptotriazine intermediates by alkylation with methyl iodide under basic conditions. For example, the reaction of 4,4'-dichlorobenzil with thiosemicarbazide provides the 5,6-bis(4-chlorophenyl)-1,2,4-triazine-3-thiol intermediate which is converted to the 3-methylmercapto derivative.

Alternatively, the benzils may be condensed with S-methylthiosemicarbazide to prepare the 3-methylmercaptotriazine derivatives directly.

The analogous pyrazine compounds are prepared in a similar manner. Yolanda T. Pratt in *Heterocyclic Compounds*, Volume 6, Part 2, John Wiley and Sons, Inc., New York, N.Y., 1957, Chapter 9, pp. 377–454, describes the preparation of 5,6-disubstituted-2-hydroxypyrazines from the appropriately substituted diones and glycine amide, as well as the subsequent transformation of the 2-hydroxypyrazines to the corresponding 2-chloro analogs by reaction with phosphorous oxychloride. The 2-chloro intermediates are reacted with amines via nucleophilic displacement in the same manner as previously described for the triazine compounds.

The benzils required for the triazine and pyrazine intermediates are prepared by the oxidation of benzoins obtained from aromatic aldehydes via reaction with cyanide ion, i.e., the classic benzoin condensation [See *Organic Reactions* 4, 269 (1948)]. The resultant benzoins are oxidized to benzils with copper sulfate in pyridine as described by Clarke and Driger, *Organic Synthesis*, Coll. Vol. I, 87 (1941), for example.

Unsymmetrical benzils are obtained from mixed benzoins which arise when dissimilar aldehydes are condensed. The benzil compounds required for the preparation of the starting materials and intermediate triazines and pyrazines are represented by the formula

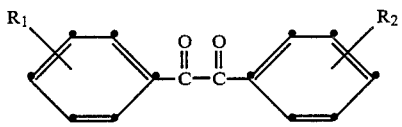

wherein $R^1$ and $R^2$ are described hereinabove. When $R^1$ and $R^2$ represent different groups the depicted benzils are unsymmetrical. The use of unsymmetrical benzil starting materials may result in the preparation of isomer mixtures of triazines or pyrazines. For example, the condensation of 4-methyl-4'-chlorobenzil with thiosemicarbazide provides a mixture of 5-(4-methylphenyl)-6-(4-chlorophenyl)-1,2,4-triazine-3-thiol and 6-(4-methylphenyl)-5-(4-chlorophenyl)-1,2,4-triazine-3-thiol.

It will be recognized by those skilled in the art that isomeric mixtures of triazines or pyrazines are separable by methods such as fractional crystallization or chromatography. The isomer separation may be effected upon intermediate mixtures or delayed until the final product stage.

The reactant amines, represented by the formula,

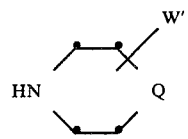

wherein Q is the same as previously defined, and W' is limited to the subgroup of hydrogen, $C_1$–$C_3$ alkyl, hydroxy, hydroxymethyl, $(-OCH_2)_2$, and $-COB$, as previously defined and limited, are employed neat, in excess, at their boiling temperatures to accomplish the nucleophilic displacements. The nucleophilic amines, in excess or molar equivalent amounts, are also used in the presence of inert solvents such as alcohols, benzene, dioxane, pyridine, toluene, chloroform, xylene and the like. Volatile amines are reacted in a sealed autoclave. In the halogen displacement of 3-chlorotriazines or 2-chloropyrazines, it is convenient to employ excess amine, since the amine also serves as the halo-acid scavenger. Acid scavengers such as pyridine, triethylamine, sodium carbonate and the like are used with a molar equivalent of the amine in an inert solvent when the amount of the amine may be an economic consideration.

Many of the amines as represented above are commercially available. Others are derivatives of commercially available amines and those skilled in the art may perform such derivatizations using the conventional methods of acylation, alkylation, aminolysis, esterification, hydrolysis, etc. Although in some cases derivatization may be performed prior to the condensation with the triazine intermediate, those skilled in the art will recognize that it is frequently easier or mandatory to perform the derivatization of the amine after the condensation with the triazine intermediate since the presence of the secondary amine functionality may hinder or prevent the desired derivatization. Still other amines are prepared by the methods known to the art, i.e., the alkylation of ammonia, the reduction of cyanides, nitro compounds and oximes, reductive alkylation, the Curtius reaction, the Gabriel amine synthesis, the Hofmann reaction, the Leuckart reaction, the Schmid reaction, etc., followed by condensation and/or derivatization in the proper order as described above.

A preferred embodiment of this novel invention consists of those compounds in which both substituted aryl groups are the same (Formula I, $R_1=R_2$). A second preferred embodiment is where the substituents on the aryl rings are in the 4-position, especially 4-chlorophenyl and 4-methylphenyl derivatives. With respect to the substituent in the 3-position of the triazine ring or the 2-position of the pyrazine ring, the preferred groups are those in which a hydroxy or especially an acyloxy group is the substituent on the amine ring, derivatives of the 4-hydroxypiperidine ring (Q is $CH_2$) being most preferred.

Representative of this invention are the following compounds:
1-[5,6-bis(4-methylphenyl)-pyrazin-2-yl]-4-piperidinol,
1-[5,6-bis(4-methylphenyl)-1,2,4-triazin-3-yl]-4-piperidinol,
1-[5-(4-methylphenyl)-6-(4-chlorophenyl)-1,2,4-triazin-3-yl]-4-piperidinol,
1-[5-(4-chlorophenyl)-6-(4-methylphenyl)-1,2,4-triazin-3-yl]-4-piperidinol,
1-[5,6-bis(4-chlorophenyl)-1,2,4-triazin-3-yl]-3-pyrrolidinol, 1-[5-(2-methylphenyl)-6-(4-methylpheny)-1,2,4-triazin-3-yl]-3-piperidinol,
1-[5-(2-chlorophenyl)-6-(3-ethylphenyl)-1,2,4-triazin-3-yl]-4-piperidinol,
1-[5-(4-isopropylphenyl)-6-(3-chlorophenyl)-1,2,4-triazin-3-yl]-4-piperidinol, benzoate (ester),
1-[5,6-bis(4-methylphenyl)-1,2,4-triazin-3-yl]-4-piperidinol, acetate (ester),
1-[5,6-bis(4-chlorophenyl)-1,2,4-triazin-3-yl]-3-piperidinol, acetate (ester),
1-[5-(3-methylphenyl)-6-(3-n-propylphenyl)-1,2,4-triazin-3-yl]-4-piperidinol, t-butanoate (ester),
B  1-[5-(2-ethylphenyl)-6-(3-chlorophenyl)-pyrazin-2-yl]-3-piperidinol, propionate (ester),
5,6-bis(2-chlorophenyl)-3-piperidinyl-1,2,4-triazine,
3-(4-ethoxy-1-piperidinyl)-5,6-bis(3-methylphenyl)-1,2,4-triazine,
2-morpholino-5,6-bis(3-chlorophenyl)-pyrazine,
1-[5,6-bis(4-isopropylphenyl)-1,2,4-triazin-3-yl]-4-piperidinone,
1-[5-(3-chlorophenyl)-6-(2-n-propylphenyl)-1,2,4-triazin-3-yl]-3-pyrrolidinone,
1-[5,6-bis(3-ethylphenyl)-pyrazin-2-yl]-4-piperidinol, diethyl carbamate (ester),
1-[5,6-bis(4-chlorophenyl)-1,2,4-triazin-3-yl]-3-piperidinol, methane sulfonate (ester),
1-[5,6-bis(4-n-propylphenyl)-pyrazin-2-yl]-4-piperidinol, propyl carbamate (ester),
1-[5,6-bis(4-chlorophenyl)-pyrazin-2-yl]-4-piperidinone, oxime,
1-[5-(2-methylphenyl)-6-(3-ethylphenyl)-1,2,4-triazin-3-yl]-3-piperidinemethanol,
1-[5-(3-chlorophenyl)-6-(4-isopropylphenyl)pyrazin-2-yl]-3-piperidinecarboxylic acid, ethyl ester,
1-[5-(3-isopropylphenyl)-6-(4-isopropylphenyl)-pyrazin-2-yl]-3-pyrrolidinecarboxylic acid, N,N-diethylamide,
1-[5,6-bis(3-methylphenyl)-1,2,4-triazin-3-yl]-4-piperidinol, formate (ester),
1-[5-(2-chlorophenyl)-6-(3-chlorophenyl)-1,2,4-triazin-3-yl]-4-piperidinecarboxylic acid, N-isopropyl amide,
1-[5,6-bis(2-methylphenyl)-pyrazin-2-yl]-3-piperidinol, 4-propylbenzene sulfonate, ester,
8-[5-(4-n-propylphenyl)-6-(3-chlorophenyl)-1,2,4-triazin-3-yl]-1,4-dioxa-8-azaspiro(4.5)decane,
1-[5,6-bis(3-n-propylphenyl)-1,2,4-triazin-3-yl]-hexahydro-1H-azepine,
1-[5,6-bis(4-ethylphenyl)-1,2,4-triazin-3-yl]-3-pyrrolidinol, propane sulfonate (ester),
1-[5-(2-methylphenyl)-6-(3-isopropylphenyl)pyrazin-2-yl]-4-propyl-hexahydro-1H-azepine,
1-[5-(4-isopropylphenyl)-6-(3-methylphenyl)-1,2,4-triazin-3-yl]-3-piperidinemethanol,
1-[5-(2-ethylphenyl)-6-(2-methylphenyl)pyrazin-2-yl]-3-hydroxy-hexahydro-1H-azepine, n-butanoate (ester),
3-(3-propoxy-1-pyrrolidinyl)-5-(2-propylphenyl)-6-(4-propylphenyl)-1,2,4-triazine,
3-morpholino-5-(4-ethylphenyl)-6-(4-isopropylphenyl)-1,2,4-triazine,
8-[5-(4-propylphenyl)-6-(4-methylphenyl)-1,2,4-triazin-3-yl]-1,4-dioxa-8-azaspiro(4.5)decane,
carbonic acid, 1-[5-(2-ethylphenyl)-6-(3-ethylphenyl)-1,2,4-triazin-3-yl]-4-piperidinyl phenyl ester,
1-[5-(4-ethyphenyl)-6-(4-n-propylphenyl)pyrazin-2-yl]-3-piperidinone,
1-[5-(4-n-propylphenyl)-6-(3-ethyphenyl)pyrazin-2-yl]-3-pyrrolidinecarboxamide,
carbonic acid, 1-[5-(4-isopropylphenyl)-6-(2-ethylphenyl)-pyrazin-2-yl]-3-pyrrolidinyl phenyl ester,
1-[5-(3-isopropylphenyl)-6-(3-propylphenyl)pyrazin-2-yl]-4-piperidinol, acetate (ester), and
1-[5-(3-propylphenyl)-6-(4-isopropylphenyl)pyrazin-2-yl]-3-piperidinol, formate (ester).

The following examples illustrate the preparations of the novel compounds of this invention.

EXAMPLE 1

Preparation of 3-methylmercapto-5,6-bis(4-methylphenyl)-1,2,4-triazine

A. The above compound was prepared as taught in U.S. Pat. No. 4,013,654 (Example 3) or U.S. Pat. No. 4,018,923 (Example 3) by methylating the intermediate 3-mercapto derivative obtained from the reaction of thiosemicarbazide and 4,4′-dimethylbenzil.

B. The above compound was alternatively prepared in the following manner: To a solution of 500 g. (2.09 m.) of 4,4′-dimethylbenzil in 3 liters of methanol was added 512 g. (2.2 m.) of S-methyl-thiosemicarbazide hydroiodide (prepared from the action of methyl iodide on thiosemicarbazide in methanol), and 184.8 g. (2.2 m.) of sodium bicarbonate. After stirring for 18 hours at room temperature, the yellow precipitate was separated by filtration, washed with one liter of water, and oven dried for 12 hours, yielding 679.3 g. (100% yield) of the desired product, m.p. about 169°–170° C.

Analysis: $C_{18}H_{17}N_3S$; Calc: C, 70.33; H, 5.57; N, 13.67; Found: C, 70.04; H, 5.75; N, 13.71.

EXAMPLES 2–4

The following compounds were prepared by the method of Example 1(B) using the appropriate substituted benzil and S-methyl-thiosemicarbazide.

3-methylmercapto-5,6-bis[2-methylphenyl]-1,2,4-triazine, m.p. about 109.5°–110.0° C.

Analysis: $C_{18}H_{17}N_3S$; Calc: C, 70.33; H, 5.57; N, 13.67; Found: C, 70.57; H, 5.31; N, 13.48.

3-methylmercapto-5,6-bis[3-methylphenyl]-1,2,4-triazine, m.p. about 87°–89° C.

3-methylmercapto-5,6-bis[4-ethylphenyl]-1,2,4-triazine, m.p. about 90°–91° C.

Analysis: $C_{20}H_{21}N_3S$; Calc: C, 71.61; H, 6.31; N, 12.53; S, 9.56; Found: C, 71.31; H, 6.16; N, 12.31; S, 9.84.

EXAMPLE 5

Preparation of 3-methylmercapto-5,6-bis[4-chlorophenyl]-1,2,4-triazine

Following the procedures as taught in U.S. Pat. No. 4,013,654 (Example 3) and U.S. Pat. No. 4,018,923 (Example 3), 3-mercapto-5,6-bis(4-chlorophenyl)-1,2,4-triazine was treated with methyl iodide in the presence of sodium hydroxide and ethanol to give 3-methylmercapto-5,6-bis[4-chlorophenyl]-1,2,4-triazine, m.p. 125.5°–128° C. (crystallized from 2B alcohol).

Analysis: $C_{16}H_{11}N_3Cl_2S$; Calc: C, 55.18; H, 3.18; N, 12.07; Found: C, 55.57; H, 3.17; N, 12.29.

EXAMPLE 6

Preparation of 3-chloro-5,6-bis(4-methylphenyl)-1,2,4-triazine

In a manner similar to that described for the bis(4-chlorophenyl) analog (see U.S. Pat. No. 3,989,831, Example 3), 100.0 g. (0.36 m.) of 3-hydroxy-5,6-bis(4-methylphenyl)-1,2,4-triazine were allowed to reflux in 100 ml. of phosphorus oxychloride for about two hours. After cooling, the solution was slowly poured onto crushed ice. The resulting precipitate was extracted into ethyl acetate which was then washed twice with water and once with 2% aqueous sodium hydroxide. The organic solution was dried over anhydrous sodium sulfate, filtered, and evaporated in vacuo. The resulting oil was triturated with Skelly B/cyclohexane and filtered. The filtrate was treated with decolorizing carbon, filtered, and evaporated to give 37.4 g. (35.2% yield) of the title compound, m.p. about 126.5°–129.5° C.

Analysis: $C_{17}H_{14}N_3Cl$; Calc: C, 69.04; H, 4.77; N, 14.21; Cl, 11.99; Found: C, 68.85; H, 4.99; N, 14.04; Cl, 11.70.

EXAMPLE 7

Preparation of 1-[5,6-bis(4-methylphenyl)-1,2,4-triazin-3-yl]-4-piperidinol

A solution of 150 g. (0.488 m.) of 3-methylmercapto-5,6-bis(4-methylphenyl)-1,2,4-triazine was heated at about 150° C. for 20 hours in 100 g. (0.99 m.) of 4-hydroxypiperidine. The solution was added to crushed ice, a small amount of ethanol was added, and the suspension was stirred for 2 hours. The yellow solid was isolated by filtration and dried. On crystallization from 550 ml. 2B ethanol and 100 ml. water, 167 g. (95.1% yield) of the desired product was obtained, m.p. about 167°–168.5° C.

Analysis: $C_{22}H_{24}N_4O$; Calc: C, 73.31; H, 6.71; N, 15.54; Found: C, 73.34; H, 6.71; N, 15.50.

EXAMPLE 8

Preparation of 1-[5,6-bis(4-ethylphenyl)-1,2,4-triazin-3-yl]-4-piperidinol

Following the procedure in Example 7, 38.45 g. (0.115 m.) of 3-methylmercapto-5,6-bis(4-ethylphenyl)-1,2,4-triazine were reacted with 23.22 g. of 4-hydroxypiperidine to give 29.1 g. (65.3% yield) of the desired product, m.p. about 164.5°–166.5° C.

Analysis: $C_{24}H_{28}N_4O$; Calc: C, 74.20; H, 7.26; N, 14.42; Found: C, 74.21; H, 7.22; N, 14.36.

EXAMPLE 9

Preparation of 1-[5,6-bis(2-methylphenyl)-1,2,4-triazin-3-yl]-4-piperidinol

Following the procedure in Example 7, 29 g. (0.095 m.) of 3-methylmercapto-5,6-bis(2-methylphenyl)-1,2,4-triazine were reacted with 46.5 g. of 4-hydroxypiperidine to give 27.8 g. (81.3% yield) of the desired product, m.p. about 155.0°–155.5° C.

Analysis: $C_{22}H_{24}N_4O$; Calc: C, 73.31; H, 6.71; N, 15.54; Found: C, 73.19; H, 6.44; N, 15.25.

EXAMPLE 10

Preparation of 1-[5,6-bis(3-methylphenyl)-1,2,4-triazin-3-yl]-4-piperidinol

Following the procedure in Example 7, 44.3 g. (0.14 m.) of 3-methylmercapto-5,6-bis(3-methylphenyl)-1,2,4-triazine were reacted with 29.2 g. of 4-hydroxypiperidine to give the desired product, m.p. about 60° C.

Analysis: $C_{22}H_{24}N_4O$; Calc: C, 73.31; H, 6.71; N, 15.54; Found: C, 73.51; H, 6.96; N, 15.35.

EXAMPLE 11

Preparation of 1-[5,6-bis(4-chlorophenyl)-1,2,4-triazin-3-yl]-4-piperidinol

Following the procedure in Example 7, 18.4 g. (0.053 m.) of 3-methylmercapto-5,6-bis(4-chlorophenyl)-1,2,4-triazine were reacted with 13.13 g. of 4-hydroxypiperidine to give 3.51 g. (16.6% yield) of the desired product, m.p. about 102°–105° C.

Analysis: $C_{20}H_{28}N_4OCl_2$; Calc: C, 59.86; H, 4.52; N, 13.96; Found: C, 59.71; H, 4.52; N, 13.68.

EXAMPLES 12–14

Preparation of acetate derivatives

Some of the hydroxypiperidine compounds of this invention were acetylated in the usual manner.

For example, 20 g. (0.055 m.) of 1-[5,6-bis(4-methylphenyl)-1,2,4-triazin-3-yl]-4-piperidinol were refluxed with 70 ml. of pyridine and 160.9 g. of acetic anhydride for 4 hours. After cooling and concentration, ethanol and water were added, and the solution evaporated. Recrystallization from ethanol-water yielded 21.8 g. (98.2% yield) of 1-[5,6-bis(4-methylphenyl)-1,2,4-triazin-3-yl]-4-piperidinol, acetate (ester), m.p. about 124°–126° C.

Analysis: $C_{24}H_{26}N_4O_2$; Calc: C, 71.62; H, 6.51; N, 13.92; Found: C, 71.81; H, 6.31; N, 13.78.

In the same manner was prepared 1-[5,6-bis[4-chlorophenyl]-1,2,4-triazin-3-yl]-4-piperidinol, acetate (ester)

Analysis: $C_{22}H_{20}N_4O_2Cl_2$; Calc: C, 59.60; H, 4.55; N, 12.64; Found: C, 59.82; H, 4.68; N, 12.43.

In the same manner was prepared 1-[5,6-bis(2-methylphenyl)-1,2,4-triazin-3-yl]-4-piperidinol, acetate (ester).

Analysis: $C_{24}H_{26}N_4O_2$; Calc: C, 71.62; H, 6.51; N, 13.92; Found: C, 71.85; H, 6.70; N, 13.91.

EXAMPLE 15

Preparation of 1-[5,6-bis(4-methylphenyl)-1,2,4-triazin-3-yl]-4-piperidinol, propanoate (ester)

According to the same general procedure for acetate preparation, 10.0 g. (0.027 m.) of 1-[5,6-bis(4-methylphenyl)-1,2,4-triazin-3-yl]-4-piperidinol, 165.1 g. of propionic anhydride, and 35 ml. of pyridine were reacted to give 8.8 g. (78.3% yield) of the desired product, m.p. about 136°–138° C.

Analysis: $C_{25}H_{28}N_4O_2$; Calc: C, 72.09; H, 6.78; N, 13.45; Found: C, 72.35; H, 6.50 N, 13.56.

EXAMPLE 16

Preparation of 1-[5,6-bis(4-methylphenyl)-1,2,4-triazin-3-yl]-4-piperidinol, pivaloate (ester)

To 40 ml. of pyridine was added 5.0 g. (0.014 m.) of 1-[5,6-bis(4-methylphenyl)-1,2,4-triazin-3-yl]-4-piperidinol followed by the dropwise addition of 39.3 g (0.328 m.) of pivaloyl chloride. The solution was heated to reflux for 4 hours. On cooling, the solution was poured onto crushed ice and extracted into ethyl acetate. The organic solution was washed twice with 5% aqueous sodium bicarbonate, once with water, dried with anhydrous sodium sulfate, filtered and concentrated. The concentrate was treated with hot ethyl acetate and decolorizing carbon. After filtration the solution was concentrated to an oil. The oil was chromatographed to provide the pure desired product, m.p. about 130°–132° C.

Analysis: $C_{27}H_{32}N_4O_2$; Calc: C, 72.94; H, 7.26; N, 12.60; Found: C, 72.92; H, 7.14; N, 12.46.

EXAMPLE 17

Preparation of 1-[5,6-bis(4-methylphenyl)-1,2,4-triazin-3-yl]-4-piperidinol, benzoate (ester)

Following the procedure in Example 16, 5.0 g. (13.8 millimoles) of 1-[5,6-bis(4-methylphenyl)-1,2,4-triazin-3-yl]-4-piperidinol were allowed to react with 70 g. (0.5 m.) of benzoyl chloride in 35 ml. of pyridine to give 2.6 g. (40.3% yield) of the desired product, m.p. about 171°–173° C.

Analysis: $C_{29}H_{28}N_4O_2$; Calc: C, 74.98; H, 6.08; N, 12.06; Found: C, 74.66; H, 6.06; N, 11.88.

EXAMPLE 18

Preparation of 1-[5,6-bis(4-methylphenyl)-1,2,4-triazin-3-yl]-3-pyrrolidinol

A solution of 8.7 g. (0.029 m.) of 3-chloro-5,6-bis(4-methylphenyl)-1,2,4-triazine and 5.05 g. (0.058 m.) of 3-pyrrolidinol in 250 ml. of chloroform was allowed to reflux overnight. The solution was then poured onto crushed ice which was then extracted with 600 ml. of methylene chloride. The organic layer was washed once with 600 ml. of water, then dried over anhydrous sodium sulfate, filtered and evaporated. The residue was crystallized from ethanol-water to give 9.3 g. (92.4% yield) of the desired compound, m.p. about 147°–150° C.

Analysis: $C_{21}H_{24}N_4O$; Calc: C, 72.39; H, 6.94; N, 16.08; Found: C, 72.45; H, 6.70; N, 15.83.

EXAMPLE 19

Preparation of 1-[5,6-bis(4-methylphenyl)-1,2,4-triazin-3-yl]-3-pyrrolidinol, acetate (ester)

The reaction of 4.91 g. (0.014 m.) of 1-[5,6-bis(4-methylphenyl)-1,2,4-triazin-3-yl]-3-pyrrolidinol with acetic anhydride according to the procedure of Example 12 gave 4.9 g. (89.3% yield) of the desired product.

Analysis: $C_{23}H_{28}N_4O_2$; Calc: C, 71.11; H, 6.23; N, 14.42; Found: C, 70.86; H, 6.32; N, 14.12.

EXAMPLE 20

Preparation of 5,6-bis(4-methylphenyl)-3-(1-piperidinyl)-1,2,4-triazine

The reaction of 15.0 g. (0.05 m.) of 3-chloro-5,6-bis(4-methylphenyl)-1,2,4-triazine with 7.0 g. (0.08 m.) of piperidine according to the procedure in Example 18 gave 8.6 g. (49.2% yield) of the desired product, m.p. about 141°–143° C.

Analysis: $C_{22}H_{24}N_4$; Calc: C, 76.71; H, 7.02; N, 16.27; Found: C, 76.44; H, 7.10; N, 15.98.

EXAMPLE 21

Preparation of 1-[5,6-bis(4-methylphenyl)-1,2,4-triazin-3-yl]-hexahydro-1H-azepine The reaction of 8.0 g. (0.027 m.) of 3-chloro-5,6-bis(4-methylphenyl)-1,2,4-triazine with 5.35 g. (0.054 m.) of hexamethylenimine according to the procedure in Example 18 gave 6.0 g. (62.5% yield) of the desired product, m.p. about 162.5°–164° C.

Analysis: $C_{23}H_{26}N_4$; Calc: C, 77.06; H, 7.31; N, 15.63; Found: C, 76.83; H, 7.44; N, 15.39.

EXAMPLE 22

Preparation of 3-morpholino-5,6-bis(4-methylphenyl)-1,2,4-triazine

The reaction of 7.5 g. (0.024 m.) of 3-methylmercapto-5,6-bis(4-methylphenyl)-1,2,4-triazine with 75 ml. of morpholine according to the procedure in Example 7 gave 4.7 g. (55.7% yield) of the desired product, m.p. about 190°–192.5° C.

Analysis: $C_{21}H_{22}N_4O$; Calc: C, 72.81; H, 6.40; N, 16.17; Found: C, 73.08; H, 6.12; N, 15.98.

EXAMPLE 23

Preparation of 1-[5,6-bis(4-methylphenyl)-1,2,4-triazin-3-yl]-3-piperidinol

The reaction of 15.0 g. (0.05 m.) of 3-chloro-5,6-bis(4-methylphenyl)-1,2,4-triazine with 10.0 g. (0.1 m.) of 3-hydroxypiperidine according to the procedure in Example 18 gave 15.7 g. (87.2% yield) of the desired product, m.p. about 122°–125° C.

Analysis: $C_{22}H_{24}N_4O$; Calc: C, 73.31; H, 6.71; N, 15.54; Found: C, 73.19; H, 7.00; N, 15.74.

EXAMPLE 24

Preparation of 1-[5,6-bis(4-methylphenyl)-1,2,4-triazine-3-yl]-3-piperidinol, acetate (ester)

The acetate derivative was prepared according to the procedure of Example 12 in 89.7% yield, m.p. about 162°–163.5° C.

Analysis: $C_{24}H_{26}N_4O_2$; Calc: C, 71.62; H, 6.51; N, 13.92; Found: C, 71.42; H, 6.73; N, 13.70.

EXAMPLE 25

Preparation of 5,6-bis(4-methylphenyl)-3-(4-methyl-1-piperidinyl)-1,2,4-triazine Following the procedure of Example 18, 8.0 g. (0.027 m.) of 3-chloro-5,6-bis(4-methylphenyl)-1,2,4-triazine were reacted with 5.35 g. (0.054 m.) of 4-methylpiperidine to give 5.3 g. (54.9% yield) of the desired product, m.p. about 140°–142° C.

Analysis: $C_{23}H_{24}N_4$; Calc: C, 77.50; H, 6.79; N, 15.72; Found: C, 77.80, H, 7.00; N, 15.64.

EXAMPLE 26

Preparation of 3-(4-methoxy-1-piperidinyl)-5,6-bis(4-methylphenyl)-1,2,4-triazine To 1.3 grams of a 50% sodium hydride dispersion in oil in 180 ml. dry toluene was added 10.0 g. (0.27 m.) of 1-[5,6-bis(4-methylphenyl)-1,2,4-triazin-3-yl]-4-piperidinol. With stirring, 4.3 g. (0.03 m.) of methyl iodide were introduced to the reaction mixture and the reaction was brought to reflux. After cooling, an additional equivalent (4.3 g.) of methyl iodide was added and the reaction mixture was stirred at room temperature overnight. The solution was added to ice water and extracted with ethyl acetate. The extract was washed with water, 10% sodium hydroxide, and water, dried over anhydrous sodium sulfate and evaporated to dryness. Silica gel chromatography and crystallization from hexane gave 3.3 g. (31.8% yield) of the desired product, m.p. about 120°–121° C.

Analysis: $C_{23}H_{26}N_4O$; Calc: C, 73.77; H, 7.00; N, 14.96; Found: C, 73.66; H, 6.86; N, 14.75.

EXAMPLE 27

Preparation of 3-(4-ethoxy-1-piperidinyl)-5,6-bis(4-methylphenyl)-1,2,4-triazine Following the procedure in Example 26 using ethyl iodide, the desired product was obtained in about a 3% yield, m.p. about 124°–126° C.

Analysis: $C_{24}H_{28}N_4O$; Calc: C, 74.20; H, 7.26; N, 14.42; Found: C, 74.10; H, 7.00; N, 14.47.

EXAMPLE 28

Preparation of carbonic acid, 1-[5,6-bis(4-methylphenyl)-1,2,4-triazin-3-yl]-4-piperidinyl phenyl ester Following the procedure in Example 16, 15.0 g. (0.041 m.) of 1-[5,6-bis(4-methylphenyl)-1,2,4-triazin-3-yl]-4-piperidinol were reacted with 12.8 g. (0.082 m.) of phenyl chloroformate to give 11.3 g. (57.9% yield) of the desired product, m.p. about 141.5°–143° C.

Analysis: $C_{29}H_{28}N_4O_3$; Calc: C, 72.48; H, 5.87; N, 11.66; Found: C, 72.27; H, 6.07; N, 11.38.

EXAMPLES 29–31

Preparation of carbamate derivatives

Carbamate derivatives were prepared by direct aminolysis. The product from Example 28 (5.54 g., 0.011 m.) was stirred overnight with 100 ml. of anhydrous ammonia in 80 ml. of ethanol. The solution was then evaporated, and the residue dissolved in ether. The ether solution was washed with water, with 0.1N sodium hydroxide, with water, and then dried over anhyrous sodium sulfate and evaporated. Crystallization from ethyl acetate/Skelly B gave pure 1-[5,6-bis(4-methylphenyl)-1,2,4-triazin-3-yl]-4-piperidinol, carbamate (ester), m.p. about 183°–185° C.

Analysis: $C_{23}H_{25}N_5O_2$; Calc: C, 68.47; H, 6.25; N, 17.36; Found: C, 68.25; H, 6.45; N, 17.15.

Using the same procedure and methylamine instead of ammonia, 1-[5,6-bis(4-methylphenyl)-1,2,4-triazin-3-yl]-4-piperidinol, N-methyl carbamate (ester) was prepared, m.p. about 138°–139.5° C.

Analysis: $C_{24}H_{27}N_5O_2$; Calc: C, 69.04; H, 6.52; N, 16.77; Found: C, 68.80; H, 6.51; N, 16.54.

Using the same procedure and dimethylamine, 1-[5,6-bis(4-methylphenyl-1,2,4-triazin-3-yl]-4-piperidinol, N,N-dimethylcarbamate (ester) was prepared, m.p. about 162°–163.5° C.

Analysis: $C_{25}N_{29}N_5O_2$; Calc: C, 69.58; H, 6.77; N, 16.23; Found: C, 69.50; H, 7.03; N, 15.93.

EXAMPLE 32

Preparation of 1-[5,6-bis(4-methylphenyl)-1,2,4-triazin-3-yl]-4-piperidinol, methane sulfonate (ester)

Following the procedure in Example 16 using methanesulfonyl chloride, the desired product was prepared, m.p. about 174°–177° C.

Analysis: $C_{23}H_{26}N_4O_3S$; Calc: C, 62.99; H, 5.98; N, 12.78; Found: C, 62.87; H, 5.73; N, 12.54.

EXAMPLE 33

Preparation of 1-[5,6-bis(4-methylphenyl)-1,2,4-triazin-3-yl]-4-piperidinol, 4-methylbenzene sulfonate (ester)

Following the procedure in Example 16 using p-toluenesulfonyl chloride, the desired product was prepared, m.p. about 132°–134° C.

Analysis: $C_{29}H_{30}N_4O_3S$; Calc: C, 67.68; H, 5.88; N, 10.89; Found: C, 67.41; H, 5.62; N, 10.68.

EXAMPLE 34

Preparation of 1-[5,6-bis(4-methylphenyl)-1,2,4-triazin-3-yl]-4-piperidinol, formate (ester)

Ten grams (0.02 m.) of 1-[5,6-bis(4-methylphenyl)-1,2,4-triazine-3-yl]-4-piperidinol were heated to 95° C. in 50 ml. of 98% formic acid for 50 minutes. Work up of the reaction mixture following the procedure in Example 7 and crystallization from Skelly B/ethyl acetate gave 6.8 g. (65.3% yield) of the desired product, m.p. about 119°–121° C.

Analysis: $C_{23}H_{24}N_4O_2$; Calc: C, 71.11; H, 6.23; N, 14.42; Found: C, 70.91; H, 6.40; N, 14.22.

EXAMPLE 35

Preparation of 1-[5,6-bis(4-methylphenyl)-1,2,4-triazin-3-yl]-4-piperidinecarboxylic acid, ethyl ester Following the procedure in Example 18 using ethyl isonipecotate, the desired product was prepared, m.p. about 102°–104° C.

Analysis: $C_{25}H_{28}N_4O_2$; Calc: C, 72.09; H, 6.79; N, 13.45; Found: C, 71.84; H, 6.61; N, 13.28.

EXAMPLE 36

Preparation of 1-[5,6-bis(4-methylphenyl)-1,2,4-triazin-3-yl]-4-piperidinecarboxamide Following the procedure in Example 18 using isonipecotamide, the desired product was prepared, m.p. about 222°–223.5° C.

Analysis: $C_{23}H_{25}N_5O$; Calc: C, 71.29; H, 6.50; N, 18.07; Found: C, 71.57; H, 6.69; N, 17.80.

EXAMPLE 37

Preparation of 1-[5,6-bis(4-methylphenyl)-1,2,4-triazin-3-yl]-4-piperidinemethanol Following the procedure in Example 7 using 4-piperidine carbinol, the desired product was prepared, m.p. about 152°–153.5° C.

Analysis: $C_{23}H_{26}N_4O$; Calc: C, 73.77; H, 7.00; N, 14.96; Found: C, 73.52; H, 7.22; N, 14.68.

EXAMPLE 38

Preparation of 8-[5,6-bis(4-methylphenyl)-1,2,4-triazin-3-yl]-1,4-dioxa-8-azaspiro(4.5)decane Following the procedure in Example 18 using 1,4-dioxa-8-azaspiro[4.5]decane gave the desired product, m.p. about 169°–170° C.

Analysis: $C_{24}H_{26}N_4O_2$; Calc: C, 71.62; H, 6.51; N, 13.92; Found: C, 71.34; H, 6.50; N, 13.79.

EXAMPLE 39

Preparation of
1-[5,6-bis(4-methylphenyl)-1,2,4-triazin-3-yl]-4-piperidinone

Treatment of 2.0 g. (0.005 m.) of 8-[5,6-bis(4-methylphenyl)-1,2,4-triazin-3-yl]-1,4-dioxa-8-azaspiro[4.5]decane with 15 ml. of 90% formic acid for 15 minutes, evaporation of the solution and crystallization of the residue from isopropyl alcohol gave 1.5 g. (84.2% yield) of the desired product, m.p. about 197°-199° C.

Analysis: $C_{22}H_{22}N_4O$; Calc: C, 73.72; H, 6.19; N, 15.63; Found: C, 74.00; H, 6.22; N, 15.53.

EXAMPLE 40

Preparation of
1-[5,6-bis(4-methylphenyl)-1,2,4-triazin-3-yl]-4-piperidinone, oxime The piperidinone derivative prepared as in Example 39 (18 g.,0.05 m.) was slurried in 100 ml. of ethanol. The slurry was slowly added to a solution of 3.64 g. (0.052 m.) of hydroxyl amine hydrochloride, 2.12 g. (0.052 m.) of sodium hydroxide, 10 ml. of water, and 100 ml. of ethanol. After heating at 50° C. for 3 hours, the reaction mixture was cooled. The resulting precipitate was filtered off and crystallized first from ethanol, then from ethyl acetate, giving the desired product, m.p. about 179°-181° C.

Analysis: $C_{22}H_{23}N_5O$; Calc: C, 70.76; H, 6.21; N, 18.75; Found: C, 70.55; H, 5.99; N, 18.93.

EXAMPLE 41

Preparation of
2-chloro-5,6-bis(4-methylphenyl)-pyrazine

A. 2-hydroxy-5,6-bis(4-methylphenyl)-pyrazine

To a refluxing solution of 85.6 g. (0.36 m.) of 4,4'-dimethylbenzil and 40 g. (0.36 m.) of glycinamide hydrochloride in one liter of methanol was added 64 ml. (0.8 m.) of a 12.5N solution of sodium hydroxide over a 75 minute period. The solution was then refluxed for one hour. After cooling, 50 ml. of 12N hydrochloric acid was added, followed by the addition of 40 g. of dry potassium bicarbonate and about 10 ml. of water. The resulting precipitate was filtered off and crystallized from n-butanol. The filtrate of crystallization was evaporated to give 2-hydroxy-5,6-bis(4-methylphenyl)-pyrazine, m.p. about 250°-254° C.

Analysis: $C_{18}H_{16}N_2O$; Calc: C, 78.24; H, 5.84; N, 10.14; Found: C, 78.13; H, 5.56; N, 9.90.

B. 2-chloro-5,6-bis(4-methylphenyl)-pyrazine

A solution of 62.6 g. (0.226 m.) of 2-hydroxy-5,6-bis(4-methylphenyl)pyrazine and 250 ml. of phosphorous oxychloride was allowed to reflux overnight. The solution was then poured into 200 ml. of ice water and 300 ml. of ether. After filtration, the layers were separated. The aqueous layer was made basic with 28% ammonium hydroxide and then extracted with ethyl acetate. The ethyl acetate solution was dried, filtered, and concentrated. The concentrate was triturated with Skelly B and filtered. The filtrate was evaporated to give 2-chloro-5,6-bis(4-methylphenyl)pyrazine.

Analysis: $C_{18}H_{15}N_2Cl$; Calc: C, 73.34; H, 5.13; N, 9.50; Found: C, 73.21; H, 5.68; N, 9.11.

EXAMPLE 42

Preparation of
1-[5,6-bis(4-methylphenyl)pyrazin-2-yl]-4-piperidinol

Following the procedure of Example 7, 13.1 g. (0.044 m.) of 2-chloro-5,6-bis(4-methylphenyl)-pyrazine were heated to reflux in 200 ml. of toluene and 8.9 g. (0.088 m.) of 4-hydroxypiperidine for three days. After high pressure liquid chromatography (Waters Prep 500, Silica gel eluting with ethyl acetate), 6.5 g. (41.4% yield) of the title compound were recovered, m.p. about 176°-178° C.

Analysis: $C_{23}H_{25}N_3O$; Calc: C, 76.85; H, 7.01; N, 11.69; Found: C, 76.66; H, 7.01; N, 11.42.

EXAMPLE 43

Preparation of
1-[5,6-bis(4-methylphenyl)pyrazin-2-yl]-4-piperidinol, acetate (ester)

The product from Example 42 (2.6 g., 0.0072 m.) was acetylated following the procedure of Example 12. Crystallization from ethanol-water gave the desired product, m.p. about 149°-149.5° C.

Analysis: $C_{25}H_{27}N_3O_2$; Calc: C, 74.79; H, 6.78; N, 10.42; Found: C, 74.55; H, 6.97; N, 10.20.

The novel compounds of this invention were examined for their in vitro ability to activate GABA and benzodiazepine (BZ) binding. To measure the effect of a compound on GABA binding, Triton X-100 (octylphenoxy polyethoxyethanol, Rohm and Haas Co.) treated membrane protein was incubated in the presence of the compound and [$^3$H]GABA as detailed by Horng and Wong, *J. Neurochemistry*, 32 (5), 1379 (1979). To examine BZ binding, H-flunirazepam and the compounds were incubated with native membrane protein as reported by Wong, et al, *Brain Res. Bull.*, 5 (Suppl. 2), 853 (1980). The results in Table 1 are the nanomolar concentrations of compounds (by Example No.) which produced a 50 percent increase ($SC_{50}$) in GABA or BZ binding. Each result is the average of one or more tests.

TABLE 1

| Compound of Example No. | In vitro activation of GABA and benzodiazepine (BZ) binding* $SC_{50}$** | |
|---|---|---|
| | GABA | BZ |
| 7 | 900 | 700 |
| 8 | >10,000 | 3500 |
| 9 | >10,000 | >10,000 |
| 10 | NT | >10,000 |
| 11 | >10,000 | 4000 |
| 12 | 3.3 | 5.5 |
| 13 | 15 | 12 |
| 14 | 60 | 1000 |
| 15 | 10 | 19 |
| 16 | 110 | 14 |
| 17 | 500 | 1000 |
| 18 | 5000 | >10,000 |
| 19 | 43 | 60 |
| 20 | 5200 | 515 |
| 21 | 2000 | 600 |
| 22 | 875 | 1138 |
| 23 | 400 | 700 |
| 24 | 160 | 180 |
| 25 | 70 | 18 |
| 26 | 80 | 90 |
| 27 | 10 | 21 |
| 28 | 160 | 650 |
| 29 | 56 | 15 |
| 30 | 100 | 24 |
| 31 | 1 | 3 |

TABLE 1-continued

In vitro activation of GABA and benzodiazepine (BZ) binding*

| Compound of Example No. | $SC_{50}$** GABA | BZ |
|---|---|---|
| 32 | 68 | 6 |
| 33 | 8000 | 1200 |
| 34 | 13 | 10 |
| 35 | 12 | 18 |
| 36 | 800 | 8500 |
| 37 | 160 | 520 |
| 38 | >10,000 | 8000 |
| 39 | 200 | 430 |
| 40 | 1300 | 1600 |
| 42 | 1200 | 400 |
| 43 | 7 | 10 |

*For experimental detail, see text, Horng and Wong, J. Neurochemistry, 32 (5), 1379 (1979), and Wong, et. al., Brain Res. Bull., 5 (Suppl. 2) 853 (1980).
**Nanomolar concentration producing a 50% increase in binding
NT = Not tested.

Selected compounds were tested in the in vivo systems as described below and as summarized in Table 2.

Metrazole Induced Convulsion Inhibition Assay

In this assay, a compound to be tested was suspended in acacia (5%) and administered by gavage to each of three Cox standard strain albino male mice (18-24 grams) at the dose level being investigated. One hour after the oral administration, a water solution of metrazole (pentylenetetrazole) was administered by the intraperitoneal route to each mouse at a dose of 110 mg./kg. The mice were observed for one hour, during which time they were evaluated as to the degree of the metrazole induced convulsion. A score of 0 was assigned to a mouse not showing any signs of convulsant activity; a score of 1 was given to mice developing clonic convulsions; a score of 2 was given to mice showing flexor tonic convulsions; a score of 3 was given to mice showing extensor tonic convulsions; and a score of 4 was given to mice that died within the one hour. The scores of the three mice were totalled for each compound and dose level. The scores can range from 0 to 12; a score of 6 or less was interpreted as indicative of an active compound at that dose level. Values reported in Table 2 below are the minimum oral dose levels (mg./kg.) where activity as defined above was observed. For comparison purposes, it was found that 95% of saline or acacia-treated controls die under the above conditions. Diazepam shows activity in this test at about 1 mg./kg.

Electroshock Induced Convulsion Inhibition Assay

The drug administration and test conditions used in this assay were similar to those used in the metrazole induced convulsion inhibition assay above except that a 0.1 second, 50 milliampere electroshock through corneal electrodes induced the convulsion instead of metrazole. The animals were examined and evaluated immediately after the electroshock and were scored as before. The results in Table 2 are expressed as the lowest dose of each compound tested which was active as previously defined. For comparison, 18 milliamperes was usually sufficient to produce extensor tonic convulsions in about half of the control animals; at 50 milliamperes, almost all control animals died. Diazepam was active at about 1 mg./kg.

Appetite Suppression Assay

In this test, groups of three Cox standard strain albino male mice were weighed (18-24 grams) and then fasted overnight (16-18 hours). The mice were reweighed and then given the test compound in a suspension of acacia (5%) by gavage. Thirty minutes after oral administration, the mice were allowed to eat freely for one hour. After the eating period, the mice were weighed once more. The percent of weight gained (from the time the mice were given the test compound to after the feeding period) compared to weight lost during the fast period was calculated. The non-drug treated control animals gained back 35-55% of the weight lost on fasting. Any compound at the dose level tested which produced a weight gain of less than 10% was considered to be active. The results in Table 2 report the lowest dose level in which there was activity for each compound tested. Dextroamphetamine sulfate is active in this system at about 2.5 mg./kg.

Mouse Writhing Inhibition Assay

Writhing, which is characterized by contraction of the abdominal musculature, extension of the hindlegs, and rotation of the trunk, was induced in Cox standard strain albino male mice. The mice, weighing 18-24 grams, were fasted overnight and given the test compound by gavage in an acacia suspension (5%) 60 minutes before writhing was induced by the intraperitoneal administration of 55 mg./kg. of acetic acid (0.55 percent). Each treatment group consisted of 3 mice. The total number of writhes for the treatment group was determined during a 5-minute observation starting 5 minutes after acetic acid administration. Control groups had a total of 30-40 writhes per observation period. A compound which reduced the number of writhes to less than ten was considered active at that dose level. The results in Table 2 report the lowest dose level in which there was activity for each compound tested. Aspirin (acetyl salicylic acid) is active in this system at 200 mg./kg.

TABLE 2

In vivo testing of 5,6-bisaryl-triazine and -pyrazine derivatives

| Compound of Example No. | mg./kg.* Metrazole | Electro- Shock | Appetite Suppression | Mouse Writhing |
|---|---|---|---|---|
| 7 | 3.1 | <25 | 3.1 | 3.1 |
| 11 | 12.5 | >25 | 25 | >25 |
| 12 | 6.25 | 25 | 12.5 | 12.5 |
| 13 | 50 | >50 | >50 | >50 |
| 14 | 200 | >200 | 200 | >200 |
| 15 | 12.5 | 12.5 | 12.5 | >12.5 |
| 17 | >200 | >200 | >200 | >200 |
| 18 | >200 | 200 | 12.5 | 200 |
| 20 | 12.5 | 50 | 12.5 | 12.5 |
| 21 | >200 | >200 | >200 | >200 |
| 23 | 50 | 50 | 12.5 | 12.5 |
| 24 | >200 | >200 | >200 | >200 |
| 25 | >200 | >200 | 50 | >200 |
| 26 | 6.2 | 6.2 | 6.2 | 6.2 |
| 28 | >200 | >200 | >200 | >200 |
| 29 | >6.25 | >6.25 | 0.4 | 1.56 |
| 32 | >6.25 | >6.25 | 0.4 | 0.4 |
| 33 | >200 | >200 | >200 | >200 |
| 35 | >200 | >200 | >200 | >200 |
| 38 | >200 | >200 | >200 | >200 |
| 39 | 50 | 50 | 12.5 | 50 |
| 42 | 12.5 | 50 | 12.5 | 12.5 |
| 43 | 25 | 100 | 25 | 100 |

*Minimum active oral dose. Refer to text for a description of the test systems

We claim:
1. A compound of the formula

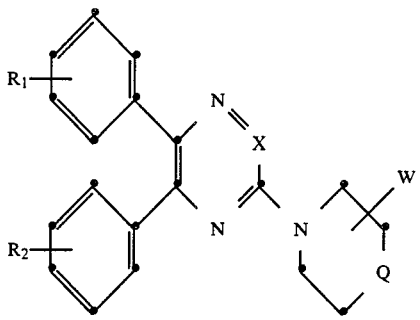

wherein
each $R_1$ and $R_2$ is independently $C_1$–$C_3$ alkyl or chloro;
X is N;
Q is oxygen or —$(CH_2)_n$—, where n is 0, 1, or 2;
W is hydrogen, $C_1$–$C_3$ alkyl, $C_1$–$C_3$ alkoxy, keto, hydroxyimino, (—$OCH_2)_2$— hydroxy, hydroxymethyl, —OCHO, —OCOA, —$OSO_2$A, or —COB, where A is $C_1$–$C_4$ alkyl, phenyl, phenoxy, amino, $C_1$–$C_3$ alkyl substituted phenyl, or mono- or di-$C_1$–$C_3$ alkyl amino, and where B is $C_1$–$C_3$ alkoxy, amino, or mono- or di-$C_1$–$C_3$ alkylamino;
subject to the limitations that when Q represents oxygen, W is limited to hydrogen, and that when Q represents —$(CH_2)_n$—, W, except when hydrogen or $C_1$–$C_3$ alkyl, is not on a carbon atom adjacent to the ring nitrogen atom.

2. A compound of claim 1 wherein the substituents $R_1$ and $R_2$ are the same.

3. A compound of claim 1 wherein $R_1$ and $R_2$ are in the 4-position.

4. A compound of claim 3 wherein $R_1$ and $R_2$ are 4-chloro.

5. A compound of claim 3 wherein $R_1$ and $R_2$ are 4-methyl.

6. A compound of claim 1 wherein Q is —$(CH_2)_n$—.

7. A compound of claim 6 wherein W is hydroxy.

8. A compound of claim 6 wherein W is —OCOA.

9. A compound of claim 1 wherein $R_1$ and $R_2$ are both 4-methyl or 4-chloro, W is hydroxy or —OCOA, and Q is —$CH_2$—.

10. The compound of claim 5 which compound is 1-[5,6-bis(4-methylphenyl)-1,2,4-triazin-3-yl]-4-piperidinol.

11. The compound of claim 4 which compound is 1-[5,6-bis(4-chlorophenyl)-1,2,4-triazin-3-yl]-4-piperidinol.

12. The compound of claim 5 which compound is 1-[5,6-bis(4-methylphenyl)-1,2,4-triazin-3-yl]-4-piperidinol, acetate (ester).

13. The compound of claim 5 which compound is 1-[5,6-bis(4-methylphenyl)-1,2,4-triazin-3-yl]-4-piperidinol, propanoate (ester).

14. The compound of claim 5 which compound is 5,6-bis(4-methylphenyl)-3-(1-piperidinyl)-1,2,4-triazine.

15. The compound of claim 5 which compound is 1-[5,6-bis(4-methylphenyl)-1,2,4-triazin-3-yl]-3-piperidinol.

16. The compound of claim 5 which compound is 3-(4-methoxy-1-piperidinyl)-5,6-bis(4-methylphenyl)-1,2,4-triazine.

17. The compound of claim 5 which compound is 1-[5,6-bis(4-methylphenyl)-1,2,4-triazin-3-yl]-4-piperidinol, carbamate (ester).

18. The compound of claim 5 which compound is 1-[5,6-bis(4-methylphenyl)-1,2,4-triazin-3-yl]-4-piperidinol, methane sulfonate (ester).

19. The compound of claim 5 which compound is 1-[5,6-bis(4-methylphenyl)-1,2,4-triazin-3-yl]-4-piperidinone.

* * * * *